(12) United States Patent
Uraki

(10) Patent No.: US 7,396,156 B2
(45) Date of Patent: Jul. 8, 2008

(54) ANALYSIS DATA GENERATING APPARATUS, ANALYSIS DATA GENERATING METHOD AND COMPUTER-READABLE RECORDING MEDIUM CONTAINING ANALYSIS DATA GENERATING PROGRAM

(75) Inventor: Yasushi Uraki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 132 days.

(21) Appl. No.: 11/523,587

(22) Filed: Sep. 20, 2006

(65) Prior Publication Data

US 2007/0274369 A1    Nov. 29, 2007

(30) Foreign Application Priority Data

May 29, 2006    (JP)    ............... 2006-148830

(51) Int. Cl.
*G01N 25/18* (2006.01)
*G06F 15/00* (2006.01)

(52) U.S. Cl. ......................... 374/44; 702/136

(58) Field of Classification Search .................. 374/43, 374/44
See application file for complete search history.

(56) References Cited

U.S. PATENT DOCUMENTS 5,416,729 A * 5/1995 Leon et al. .................... 716/20
5,671,167 A   9/1997 Ito et al. ...................... 364/578
6,438,504 B2 * 8/2002 Mikubo et al. .............. 702/132
7,347,621 B2 * 3/2008 Sri-Jayantha et al. ....... 374/166
2005/0102117 A1 * 5/2005 Habitz ......................... 702/133

FOREIGN PATENT DOCUMENTS

| JP | 8-263697   | 10/1996 |
| JP | 10-48166   | 2/1998  |
| JP | 2004-34100 | 2/2004  |

* cited by examiner

*Primary Examiner*—Gail Verbitsky
*Assistant Examiner*—Mirellys Jagan
(74) *Attorney, Agent, or Firm*—Staas & Halsey LLP

(57) ABSTRACT

The present invention has an object for setting thermal resistance corresponding to a contact condition of a contact face between two elements automatically and generating analysis data including a thermal conductivity of the contact face accurately in a short time when analysis data is generated based on three-dimensional design data of an object formed by a plurality of elements. An apparatus according to the present invention includes a retaining unit for retaining thermal resistance information for obtaining thermal resistance of the contact face in accordance with contact condition of the contact face; a thermal conductivity calculating unit for calculating a thermal conductivity of the contact face based on the thermal resistance information which is retained in the retaining unit and corresponds to the contact condition of the contact face set by a contact condition setting unit; and a generating unit for generating the analysis data including the thermal conductivity.

16 Claims, 7 Drawing Sheets

FIG. 4

| TYPE | MANUFACTURER | PRODUCT NAME | THERMAL RESISTANCE (°C/W) | THICKNESS (mm) |
|---|---|---|---|---|
| S | XXX CO. | aaa1 | 4.2 | 1.0 |
| T | XXX CO. | aaa2 | 3.3 | 0.5 |
| U | YYY CO. | bbb1 | 1.2 | 0.1 |
| V | YYY CO. | bbb2 | 1.0 | 0.5 |

FIG. 5

| CONTACT CONDITION | COEFFICIENT | FINISHING CONDITION | COEFFICIENT |
|---|---|---|---|
| SIMPLE CONTACT | 1.0 | NORMAL FINISHING | 1.0 |
| SPRING CONTACT | 0.7 | MIRRORED FINISHING | 0.01 |
| SCREWED CONTACT | 0.5 | | |

ANALYSIS DATA GENERATING APPARATUS, ANALYSIS DATA GENERATING METHOD AND COMPUTER-READABLE RECORDING MEDIUM CONTAINING ANALYSIS DATA GENERATING PROGRAM

BACKGROUND OF THE INVENTION

1) Field of the Invention

The present invention relates to a technique for generating analysis data for analyzing (for example, thermo-fluid analyzing) an object formed by a plurality of elements based on three-dimensional design data of the object.

2) Description of the Related Art

In resent years, a three-dimensional design using CAD (Computer Aided Design) has been improved in design developments of an apparatus or the like. In order to utilize the three-dimensional CAD data (hereinafter, referred to as three-dimensional design data) generated by CAD effectively, tools for converting the three-dimensional design data into analysis data (an analysis model) for analyzing (simulating) the object has been developed (for example, see Japanese Patent Application Laid-Open No. HEI 8-263697).

When an analysis model is generated automatically with the use of such a tool, the time for generating the analysis model can be significantly reduced.

Regarding an object of an apparatus or the like, since it is difficult to show a contact condition (mode) of a contact face where end faces of a plurality of elements contact with each other in the three-dimensional design data, such a contact condition is not included in the three-dimensional design data.

Here, the contact condition of the contact face between the elements represents a contact mode at the contact face where end faces of two elements contact with each other. The contact condition is indicated by a simple contact where elements simply contact with each other, a spring contact where elements are adhered to each other by a force of a spring, an adhesive contact by an adhesive material, an adhesive contact by an adhesive sheet, a connection contact by a screw, and the like.

The contact condition of the contact face between the elements has a great influence on a thermal conduction between the elements. Accordingly, when a thermo-fluid analysis (thermal conduction analysis) is implemented with the use of thermal conductivities of the elements, it is preferable to see the conduction manner of heat between the elements (that is, a thermal conductivity) in consideration of the contact condition of the contact face between the elements. This allows an implementation of a high-accuracy thermo-fluid analysis of the object.

Conventionally, for the case that an element is changed in an analysis model for implementing a casting analysis simulation, there has been a technique for searching the changed element according to a contact condition between elements and setting a thermal transferring coefficient based on the type of the element (for example, see Japanese Patent Application Laid-Open No. 2004-34100).

However, as described above, since the contact condition of the contact face between the elements is not included in the three-dimensional design data in conventional art, an operator manually sets thermal conductivities of contact faces in analysis data when a thermo-fluid analysis of an object is implemented.

Here, a conventional analysis data generating method will be explained, taking an example of generating analysis data of an object 100 based on three-dimensional design data of the object 100 shown in FIG. 9.

Since a heat sink 101, a heating element (for example, an LSI (Large Scale Integration)) 102, and a printed board 103, which constitute the object 100, have thicknesses greater than a predetermined level, they are included in the three-dimensional design data. Accordingly, the heat sink 101, the heating element 102, and the printed board 103 are automatically modeled by the above-described tool for generating analysis data from the three-dimensional design data.

However, an adhesive material 104 for connecting (adhering) the heat sink 101 and the heating element 102 is so thin (for example, about 20 µm), that it is not included in the three-dimensional design data.

Therefore, a person who implements an analysis (an operator) firstly interviews a designer of the object 100 to recognize a contact condition of a contact face (here, an adhesive area between the heat sink 101 and the heating element 102). Then, she/he inputs the thermal resistance (° C./W or K/W) of the contact face, that is, a thermal resistance of the adhesive material 104, with reference to a catalog or the like, defines the thickness of the adhesive material, obtains the dimension of the contact face, and obtains the thermal conductivity of the contact face based on the thermal resistance of the adhesive material, the thickness of the adhesive material, and the dimension of the contact face to add the thermal conductivity to the analysis data.

As described above, conventionally, the operator is required to input the thermal resistance based on the contact condition of the contact face manually in order to set the thermal conductivity of the contact face in the analysis data. Accordingly, it takes long time to generate the analysis data.

Further, since manual input by an operator is required, input errors or the like may be made, if there are a large number of elements in an object to be analyzed and a great number of contact faces between the elements. As a result, an accurate analysis data can not be generated and it may affect the accuracy of analysis results.

SUMMARY OF THE INVENTION

The present invention has been developed in view of the above problems, and has an object for automatically setting a thermal resistance corresponding to a contact condition of a contact face between two elements and generating analysis data including a thermal conductivity of the contact face accurately in a short time when the analysis data is generated based on three-dimensional design data of an object formed by a plurality of elements.

In order to achieve the object, an analysis data generating apparatus of the present invention is an apparatus for generating analysis data of an object formed by a plurality of elements from three-dimensional design data of the object, including: an extracting unit for extracting a contact face where end faces of two elements contact with each other from the three-dimensional design data; a contact condition setting unit for setting contact condition of the contact face extracted by the extracting unit; a retaining unit for previously retaining thermal resistance information to obtain thermal resistance of the contact face in accordance with the contact condition of the contact face; a thermal conductivity calculating unit for calculating a thermal conductivity of the contact face based on the thermal resistance information which is retained in the retaining unit and corresponds to the contact condition of the contact face set by the contact condition setting unit; and a generating unit for generating the analysis data including the thermal conductivity calculated by the thermal conductivity calculating unit.

Here, it is preferable that the generating unit sets the contact face extracted by the extracting unit as a thin film and generates the analysis data by associating the thin film with the thermal conductivity of the contact face.

In order to achieve the object, an analysis data generating method of the present invention is a method for generating an analysis data of an object formed by a plurality of elements from three-dimensional design data of the object, including: an extracting step for extracting a contact face where end faces of two elements contact with each other from the three-dimensional design data; a contact condition setting step for setting a contact condition of the contact face extracted at the extracting step; a thermal conductivity calculating step for calculating a thermal conductivity of the contact face based on the thermal resistance information which is previously retained in a retaining unit to obtain thermal resistance of the contact face in accordance with the contact condition of the contact face and corresponds to the contact condition of the contact face set in the contact condition setting step; and a generating step for generating the analysis data including the thermal conductivity calculated in the thermal conductivity calculating step.

In order to achieve the object, an analysis data generating program of the present invention is a program for realizing, with the use of a computer, a function for generating an analysis data of an object formed by a plurality of elements from three-dimensional design data of the object. The analysis data generating program instructs the computer to function as: an extracting unit for extracting a contact face where end faces of two elements contact with each other from the three-dimensional design data; a contact condition setting unit for setting contact condition of the contact face extracted by the extracting unit; a thermal conductivity calculating unit for calculating a thermal conductivity of the contact face based on the thermal resistance information which is previously retained in a retaining unit to obtain thermal resistance of the contact face in accordance with the contact condition of the contact face and corresponds to the contact condition of the contact face set by the contact condition setting unit; and a generating unit for generating the analysis data including the thermal conductivity calculated by the thermal conductivity calculating unit.

Further, in order to achieve the object, an analysis apparatus of the present invention is an apparatus for generating analysis data of an object formed by a plurality of elements from three-dimensional design data of the object and analyzing the object with the use of the analysis data, including: an extracting unit for extracting a contact face where end faces of two elements contact with each other from the three-dimensional design data; a contact condition setting unit for setting contact condition of the contact face extracted by the extracting unit; a retaining unit for previously retaining thermal resistance information to obtain thermal resistance of the contact face in accordance with the contact condition of the contact face; a thermal conductivity calculating unit for calculating a thermal conductivity of the contact face based on the thermal resistance information which is retained in the retaining unit and corresponds to the contact condition of the contact face set by the contact condition setting unit; a generating unit for generating the analysis data including the thermal conductivity calculated by the thermal conductivity calculating unit; and an analyzing unit for implementing the analysis with the use of the analysis data generated by the generating unit.

As described above, according to the present invention, an extracting unit extracts a contact face of an object (extracting step); a contact condition setting unit sets a contact condition of the contact face (contact condition setting step); a thermal resistivity calculating unit calculates a thermal conductivity of the contact face based on thermal resistance information which is retained in a thermal resistance information retaining unit and corresponds to the contact condition set by the contact condition setting unit (thermal conductivity calculating step); and a generating unit generates analysis data including the calculated thermal conductivity (generating step). Accordingly, when analysis data is generated based on three-dimensional design data of an object formed by a plurality of elements, a thermal resistance corresponding to a contact condition of a contact face can be set automatically and analysis data including thermal conductivity of the contact face can be generated accurately in a short time.

Further, an analyzing unit analyzes based on the analysis data generated as described above so that the analyzing unit can implement a high-accuracy thermo-fluid analysis of the object.

The generating unit sets the contact face as a thin film and generates analysis data by associating the thin film with the thermal conductivity of the contact face. Accordingly, the thermal conductivity can be included in the analysis data certainly and accurately.

BRIEF DESCRIPTION OF THE DRAWINGS

FIG. 4 is a diagram showing a structure example of a table retained in a thermal resistance information retaining unit of an analysis data generating unit in the analysis apparatus according to an embodiment of the present invention;

FIG. 5 is a diagram showing a structure example of a table retained in a thermal resistance information retaining unit of an analysis data generating unit in the analysis apparatus according to an embodiment of the present invention;

FIG. 6(a) shows a diagram of a first setting screen, and FIG. 6(b) is a diagram of a second setting screen;

FIG. 7(a) shows a diagram of a first setting screen, and FIG. 7(b) is a diagram of a third setting screen;

DESCRIPTION OF THE PREFERRED EMBODIMENTS

An embodiment of the present invention will be explained with reference to the accompanying drawings.

[1] Regarding an Embodiment of the Present Invention

Figure 1:
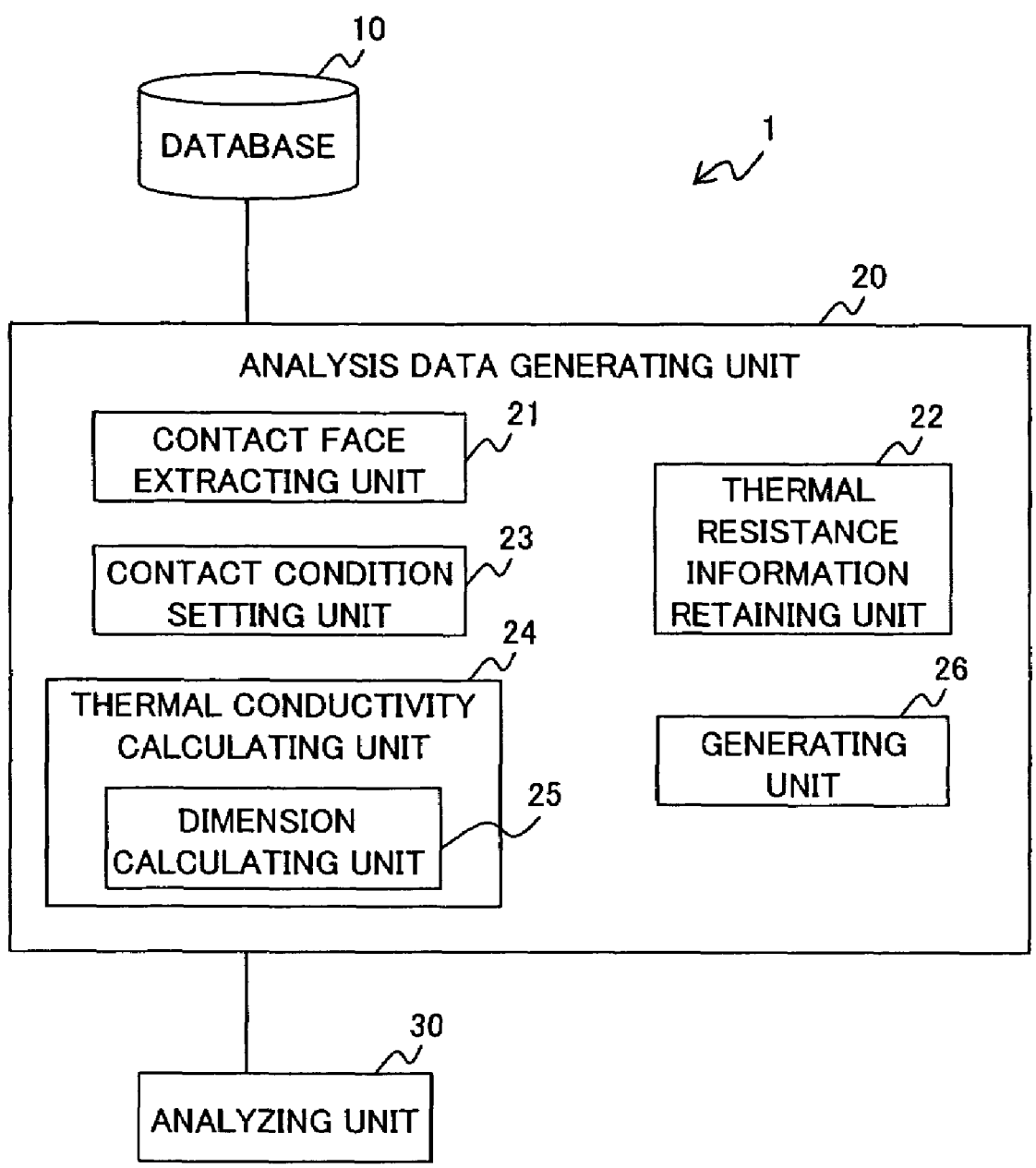
FIG. 1 is a block diagram showing a structure of an analysis apparatus according to an embodiment of the present invention.

With reference to a block diagram of FIG. 1, a structure of an analysis apparatus 1 according to an embodiment of the present invention will be described. As shown in FIG. 1, the present analysis apparatus 1 includes a database 10 for retaining three-dimensional design data of an object formed by a plurality of elements, an analysis data generating unit (analysis data generating apparatus) 20 for generating analysis data of the object from the three-dimensional design data retained in the database 10, and an analyzing unit 30 for implementing an analysis of the object with the use of the analysis data generated by the analysis data generating unit 20.

In the present analysis apparatus 1, the analyzing unit 30 implements a thermo-fluid analysis (thermal conduction analysis) of an object whose three-dimensional design data is retained in the database 10. In other words, the analyzing unit 30 implements the thermo-fluid analysis of the object with the use of analysis data generated by the analysis data generating unit 20.

Figure 2:
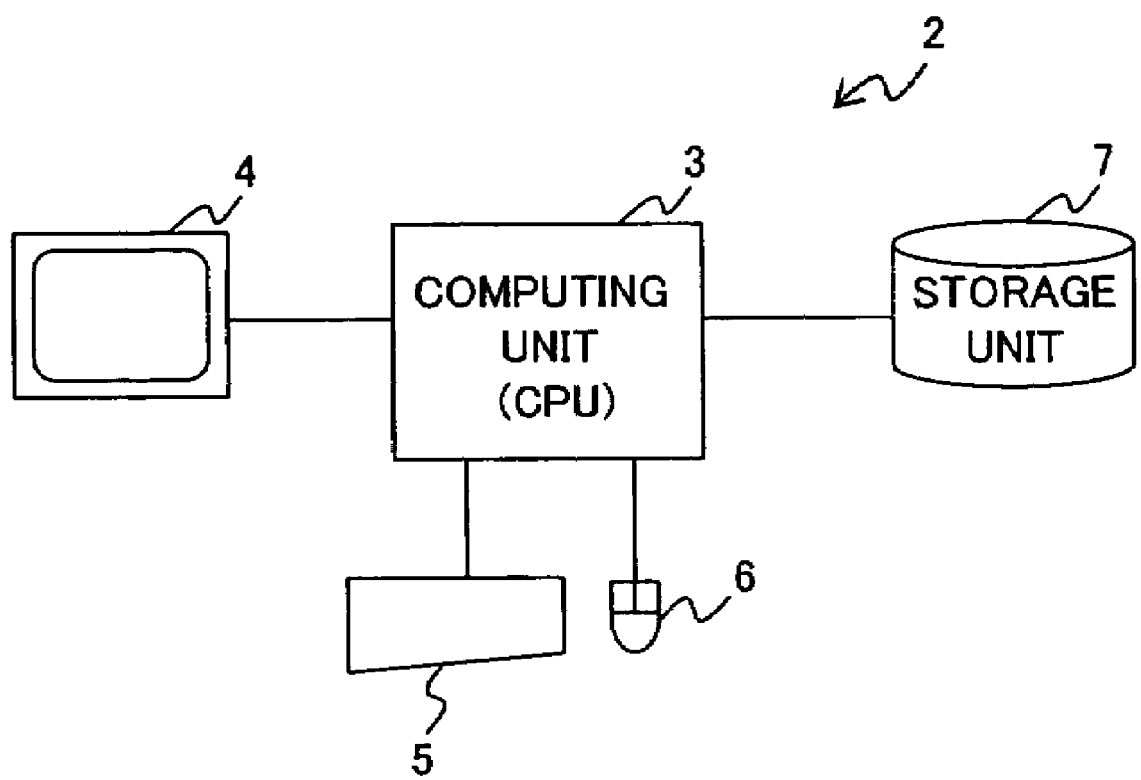
FIG. 2 is a block diagram showing an example of a structure of a computer realizing the analysis apparatus according to an embodiment of the present invention.

The present analysis apparatus 1, for example, is realized by a computer 2 composed of a computing unit (for example, CPU: Central Processing Unit) 3, a monitor 4, a keyboard 5 and a mouse 6 as input interfaces, and a storage unit 7, as shown in FIG. 2.

The database 10 of the present analysis apparatus 1 is realized by the storage unit 7. When the computing unit 3 implements a predetermined application program (a later described analysis data generating program or analyzing program), a later described contact face extracting unit 21, a contact condition setting unit 23, a thermal conductivity calculating unit 24, a generating unit 26, and an analyzing unit 30 in the analysis data generating unit 20 are realized.

Here, a later described thermal resistance information retaining unit 22 of the analysis data generating unit 20 may be realized by the storage unit 7 or by other devices such as a memory (not shown) provided in the computing unit 3.

The analysis data generating unit 20 is composed of *the contact face extracting unit (extracting unit) 21, the thermal resistance information retaining unit (retaining unit) 22, the contact condition setting unit 23, the thermal conductivity calculating unit 24, and the generating unit 26.

Taking an example in which the analysis apparatus 1 analyzes an object 40 shown in FIG. 3, the contact face extracting unit 21, the thermal resistance information retaining unit 22, the contact condition setting unit 23, the thermal conductivity calculating unit 24, and the generating unit 26 will be described in detail.

First, the object 40 will be explained. As shown in FIG. 3, the object 40 is composed of a printed board 44, on which a heating element (for example, an LSI (Large Scale Integration), hereinafter referred to as LSI) 43 having a heat sink 41 adhered by an adhesive material 42, and a heat spreader 45. The printed board 44 and the heat spreader 45 are attached to each other with a bolt 46 and a nut 47.

Here, the three-dimensional design data of the object 40 which is retained in the database 10 does not include any information about the adhesive material 42, connecting condition between the heat sink 41 and the LSI 43, or contact condition (screwed contact) between the printed board 44 and the heat spreader 45.

The contact face extracting unit 21 extracts contact faces X, Y where end faces of two elements contact with each other from the three-dimensional design data of the object 40 retained in the database 10. Here, it extracts the contact face X between an end face (lower face) of the heat sink 41 and an end face (upper face) of the LSI 43 and a contact face Y between an end face (lower face of its left end) of the printed board 44 and an end face (upper face of its right end) of the heat spreader 45. Here, the connection between the LSI 43 and the printed board 44 are not considered since it is an atypical connection.

The thermal resistance information retaining unit 22 is a library which previously retains thermal resistance information for obtaining thermal resistance of the contact faces X, Y corresponding to the contact condition of those contact faces and retains thermal resistances (values) or coefficients for calculating those thermal resistances as thermal resistance information corresponding to the contact conditions.

More specifically, the thermal resistance information retaining unit 22 retains, for example, a table 22a shown in FIG. 4. The table 22a retains, as contact conditions, thermal resistances corresponding to types (kinds) of adhesive materials S, T, U, V in case of connection (material connection) by an adhesive material or an adhesive sheet (hereinafter, referred to simply as adhesive material) and thicknesses of the contact faces corresponding to the types S, T, U, V. Further, the table 22a retains names of manufacturers and products for the adhesive materials or the like corresponding to the types S, T, U, V.

Here, corresponding to Type S as a contact condition, a name of manufacturer "XXX company," a name of product "aaa1," a thermal resistance "4.2," and a thickness "1.0" are retained. Corresponding to Type T as a contact condition, a name of manufacturer "XXX company," a name of product "aaa2," a thermal resistance "3.3," and a thickness "0.5" are retained. Corresponding to Type U as a contact condition, a name of manufacturer "YYY company," a name of product "bbb1," a thermal resistance "1.2," and a thickness "0.1" are retained. Further, corresponding to Types V as a contact condition, a name of manufacturer "YYY company," a name of product "bbb2," a thermal resistance "1.0," and thickness "0.5" are retained.

Further, the thermal resistance information retaining unit 22 retains, for example, a table 22b shown in FIG. 5. The table 22b retains, as thermal resistance information, coefficients corresponding to the contact conditions (adhesion modes; here, simple contact, spring contact, or screwed contact) which are connections without using an adhesive material or the like and coefficients corresponding to finishing conditions (surface conditions; here, normal finishing or mirrored finishing) of the element.

Here, the simple contact as the adhesion mode represents a contact condition where end faces of two elements simply contact with each other; the spring contact represents a contact condition where end faces of two elements are adhered to each other by a force of a spring; and the screwed contact indicates a contact condition where end faces of two elements are connected by a screw or a bolt with a nut.

For the simple contact as an adhesion mode, coefficient "1.0" is retained; for the spring contact as an adhesion mode, coefficient "0.7" is retained; and for the screwed contact (simply indicated as "screwed" in the drawings) as an adhesion mode, coefficient "0.5" is retained. Further, for the normal finishing as a surface condition, coefficient "1.0" is retained; and for mirrored finishing as a surface condition, coefficient "0.01" is retained.

The contact condition setting unit 23 sets contact conditions of the contact faces X, Y which are extracted by the contact face extracting unit 21. For example, the contact condition setting unit 23 sets contact conditions of the contact faces X, Y according to an instruction of an operator of the present analysis apparatus 1 (hereinafter, simply referred to as "operator") input from the keyboard 5 and the mouse 6.

Figure 6A:
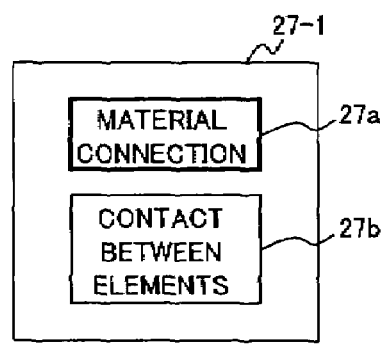
FIGS. 6(a) and 6(b) are diagrams showing setting screens of a contact condition setting unit of the analysis data generating unit in the analysis apparatus according to an embodiment of the present invention.
Figure 6B:
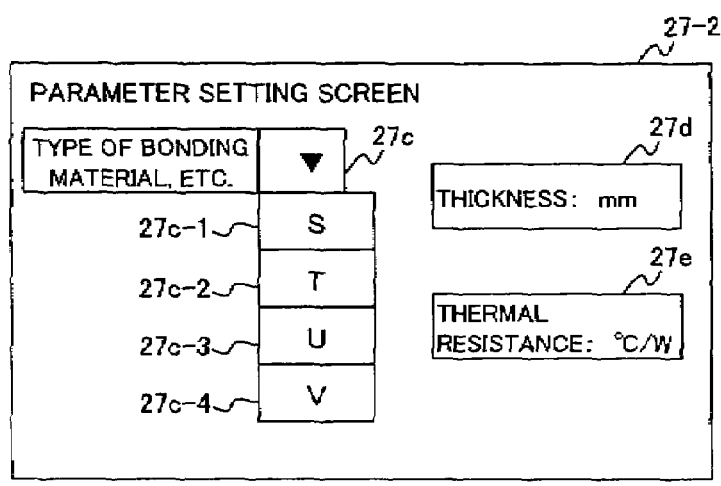

For example, the contact condition setting unit 23 firstly displays a first setting screen 27-1 composed of a material connection button 27a and an inter-element contact button 27b, as shown in FIG. 6(*a*), to let the operator set the contact condition.

Here, the contact condition set by the contact condition setting unit 23 will be explained. Firstly, the contact condition setting unit 23 sets one of the material connection or the inter-element contact as a contact condition.

The material connection is a contact condition where an end face of an element and an end face of another element are connected (adhered) by an adhesive material or a material for adhering two elements, such as an adhesive material and an adhesive sheet (hereinafter, referred to as an adhesive material).

Further, the inter-element contact is a contact condition (an adhesion mode) where an end face of an element and an end face of another element are adhered to each other by a contact without adhesive material or the like and it represents, for example, a simple contact, a spring contact, and a screwed contact.

Furthermore, the contact condition setting unit 23 sets a type (here, the types S to V) of the adhesive material or the like, among the material connections, as a contact condition.

On the other hand, the contact condition setting unit 23 sets an adhesion mode of the simple contact, the spring contact, and the screwed contact, among the inter-element contact, as a contact condition and sets finishing condition (surface condition) of the contact faces.

As described above, the contact conditions set by the contact condition setting unit 23 and the contact conditions retained in the thermal resistance information retaining unit 22 with the thermal resistance information correspond to each other.

Then, when the operator operates, for example, the mouse 6 to move a pointer on the first setting screen 27-1 shown in the monitor 4 and clicks the mouse 6 on one of desired buttons 27a, 27b, the material connection or the inter-element contact is set as a contact condition of the contact faces X, Y by the contact condition setting unit 23.

Here, a case of setting a contact condition of the contact face X will be explained. Since the contact face X is an adhered plane adhered by the adhesive material 42, the operator clicks material connection button 27a. Then, as shown in FIG. 6(*b*), the contact condition setting unit 23 displays a second setting screen (parameter setting screen) 27-2 composed of a selection button 27c, a thickness field 27d, and a thermal resistance field 27e for selecting types of adhesive material or the like on the monitor 4 to let the operator set more specific contact conditions.

Then, when the operator clicks the selection button 27c, type selecting buttons 27c-1 to 27c-4 indicating types of adhesive materials S, T, U, V are displayed. Further, one of type selecting buttons 27c-1 to 27c-4 corresponding to the adhesive material 42 is clicked, the contact condition setting unit 23 sets the type S to V indicated by the clicked button 27c-1 to 27c-4 as a contact condition of the contact face X.

When the type S to V of the adhesive material or the like is set as a contact condition by the contact condition setting unit 23, the thickness of the adhesive material is extracted by the thermal conductivity calculating unit 24 according to the table 22a in the thermal resistance information retaining unit 22. The extracted thickness is shown in the thickness field 27d on the second setting screen 27-2 and the thermal resistance of the adhesive material is shown in the thermal resistance field 27e.

On the other hand, a case for setting contact condition of the contact face Y will be explained. Since the contact face Y is a contact face where two elements are screwed by the bolt 46 and the nut 47, the operator clicks the inter-element contact button 27b on the first setting screen 27-1 as shown in FIG. 7(*a*).

Figure 7A:
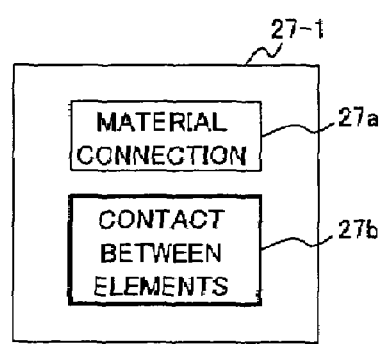
FIGS. 7(a) and 7(b) are diagrams showing setting screens of a contact condition setting unit of the analysis data generating unit in the analysis apparatus according to an embodiment of the present invention.
Figure 7B:
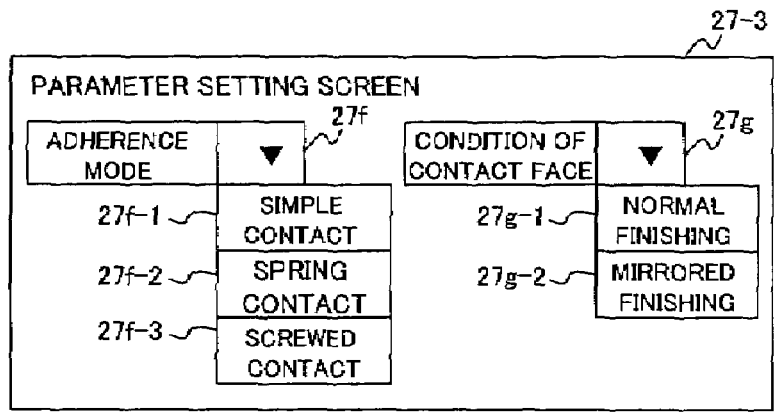

Then, as shown in FIG. 7(*b*), the contact condition setting unit 23 displays a third setting screen (parameter setting screen) 27-3 composed of a selection button 27f for selecting a more specific adhesion mode of inter-element contact and a selection button 27g for selecting a finishing condition (surface condition) of a contact face on the monitor 4 to let the operator set more specific contact conditions.

When the operator clicks the selection button 27f, condition selecting buttons 27f-1 to 27f-3 indicating the simple contact, the spring contact, and the screwed contact respectively are displayed. Further, the condition selecting button 27f-1 to 27f-3 corresponding to the contact face Y (here, the condition selecting button 27f-3 indicating the screwed contact) is clicked, the contact condition setting unit 23 sets an adhesion condition indicated by the clicked button 27f-1 to 27f-3 as a contact condition of the contact face Y.

When the operator clicks the selection button 27g, finishing selecting buttons 27g-1, 27g-2 respectively indicating a normal finishing and a mirrored finishing as finishing conditions are displayed. Furthermore, when the relevant finishing selecting button 27g-1, or 27g-2 is clicked, the contact condition setting unit 23 sets a surface condition indicated by the clicked button 27g-1, 27g-2 as a contact condition of the contact face Y.

The thermal conductivity calculating unit 24 calculates thermal conductivities for each of the contact faces X, Y based on the thermal resistance information which is retained in the thermal resistance information retaining unit 22 and corresponds to contact conditions of the contact faces X, Y set by the contact condition setting unit 23, and includes a dimension calculating unit 25.

The dimension calculating unit 25 calculates dimensions of the contact faces X, Y extracted by the contact face extracting unit 21 based on the three-dimensional design data of the object 40 retained in the database 10.

Then, the thermal conductivity calculating unit 24 extracts thermal resistance information corresponding to the contact condition, which is set by the contact condition setting unit 23, from the thermal resistance information retaining unit 22.

That is, as in the case of the contact face X, when a material connection and a type of adhesive material or the like are set by the contact condition setting unit 23, the thermal conductivity calculating unit 24 extracts thermal resistance of the type from the table 22a.

On the other hand, as in the case of the contact face Y, when an inter-element contact and more specific contact condition (adhesion mode) are set by the contact condition setting unit 23, the thermal conductivity calculating unit 24 extracts a coefficient corresponding to the contact condition from the table 22b. Then, the thermal conductivity calculating unit 24 calculates a thermal resistance based on the extracted coefficient.

That is, when the contact condition coefficient in the table 22b is "k1," the finishing condition coefficient in the table 22b is "k2," and a basic thermal resistance is "r," the thermal conductivity calculating unit 24 calculates a thermal resistance "R" by the following equation (1).

$$R = r \times k1 \times k2 \quad (1)$$

Here, the basic thermal resistance r is a thermal resistance given uniquely and, preferably, the basic thermal resistance r is set to the most ideal value.

Here, when the contact condition setting unit 23 sets a material connection with the use of an adhesive material or the like as a connecting condition and the thermal conductivity calculating unit 24 extracts thermal resistance itself from the table 22*a* in the thermal resistance information retaining unit 22, obviously, the thermal resistance will not be calculated with the use of the above equation (1).

Next, the thermal conductivity calculating unit 24 calculates thermal conductivities "λ" of the contact faces X, Y by the following equation (2) with the use of the thermal resistance R calculated by the equation (1) or the thermal resistance (hereinafter, referred to as thermal resistance R when they are not particularly distinguished) extracted from the table 22*a* in the thermal resistance information retaining unit 22, a dimension "A" calculated by the dimension calculating unit 25, and a thickness of the contact face X, Y (thickness of the contact thermal resistance model) L.

$$\lambda = L / AR \quad (2)$$

Here, the unit of the thermal conductivity λ is W/mK.

Further, since the contact faces X, Y are not included in the three-dimensional design data and their thickness are not set, the thermal conductivity calculating unit 24 sets the thickness L in order to calculate thermal conductivity of the contact faces X, Y.

Here, as in the case of the contact face X, when the contact condition setting unit 23 sets a material connection (a type of an adhesive material or the like) as a contact condition, the thickness L is extracted according to the table 22*a*. On the other hand, as in the case of the contact face Y, when the contact condition setting unit 23 sets a contact condition of an inter-element contact as a contact condition, the thickness is not extracted according to the table 22*b* so that the thermal conductivity calculating unit 24 sets the thickness L to a predetermined value.

As described above, the thermal conductivity calculating unit 24 obtains the thermal resistances of the contact faces X, Y based on the contact condition, which is set by the contact condition setting unit 23, of the contact faces X, Y, extracted by the contact face extracting unit 21, and the thermal resistance information retained in the thermal resistance information retaining unit 22. The thermal conductivity calculating unit 24 further calculates equivalent thermal conductivities of contact faces X, Y based on the obtained thermal resistances and the dimensions of the contact faces X, Y which are calculated by the dimension calculating unit 25. That is, the thermal conductivity calculating unit 24 extracts calculating parameters from the thermal resistance information retaining unit 22 in accordance with a condition given by the contact condition setting unit 23 and obtains thermal resistance to calculate the equivalent thermal conductivities.

The generating unit 26 generates analysis data including the thermal conductivity calculated by the thermal conductivity calculating unit 24. The generating unit 26 sets the contact faces X, Y extracted by the contact face extracting unit 21 as a thin film(thin film body; contact thermal resistance model) and generates analysis data by associating the thin film with equivalent thermal conductivity relevant to the contact face X, Y calculated by the thermal conductivity calculating unit 24.

In other words, since a thin layer of adhesive material 42 is generally omitted in the three-dimensional design data of the object 40, modeling of the adhesive material 42 for the contact face X of the heat sink 41 and the LSI 43 is needed in order to include thermal conductivity of the adhesive material 42 into the analysis data. Further, in order to set thermal resistance (thermal conductivity) of the contact face Y where the printed board 44 and the heat spreader 45 are connected (here, connected with a screw), modeling of the layer (thin air layer) having the thermal resistance as the contact face Y is needed.

Therefore, the generating unit 26 defines the contact faces X, Y as thin films by providing unique thickness of the contact faces X, Y. Here, the thickness of the contact faces X, Y in the analysis data may be the thickness L (see the equation (1)) set for calculating relevant thermal conductivities in the thermal conductivity calculating unit 24, or a same value may be uniquely set for all contact faces X, Y. This thickness is numeric data for setting the contact faces X, Y as thin film without considering their thicknesses in the analysis data.

Figure 8:
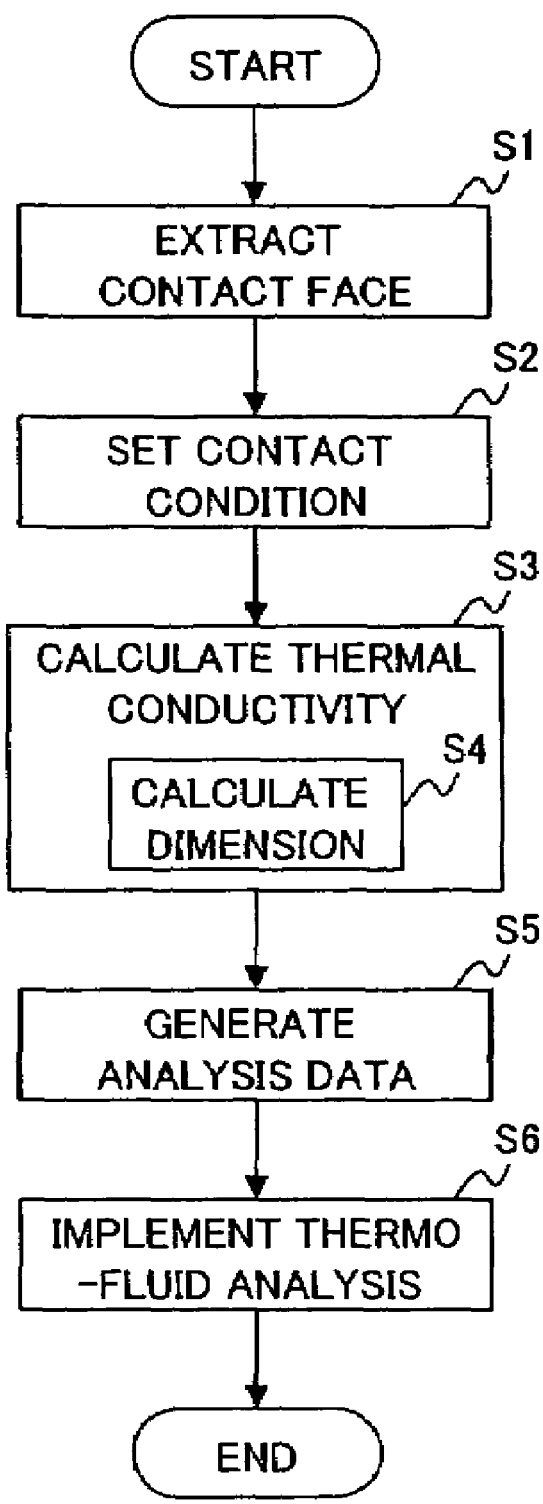
FIG. 8 is a flowchart showing an analyzing method of an embodiment of the present invention.
Figure 9:
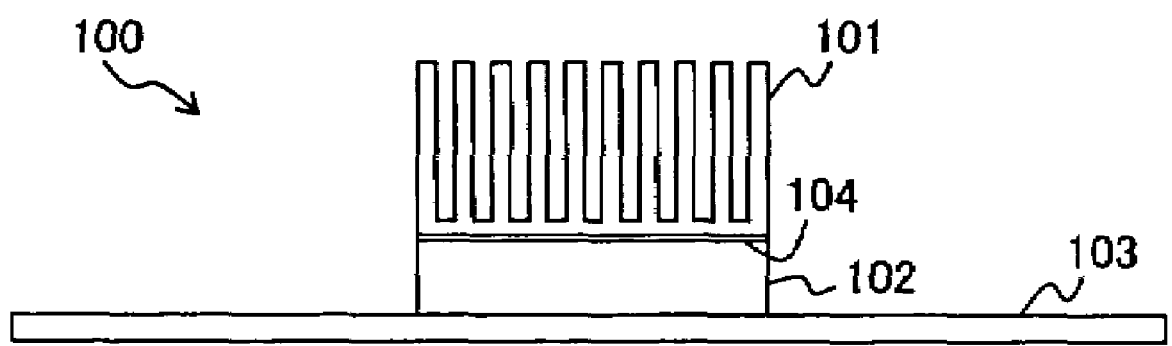
FIG. 9 is a diagram showing an example of an object as an analysis data generating subject for explaining a conventional generating technique according to a analysis data.

Next, with reference to a flowchart (steps S1 to S6) shown in FIG. 8, an operation process of the present analysis apparatus 1 (an analyzing method as an embodiment of the present invention) will be explained.

Firstly, the contact face extracting unit 21 of the analysis data generating unit 20 reads the three-dimensional design data of the object 40 from the database 10 and extracts contact faces X, Y where end faces of the two elements of the object 40 contact with each other (step S1; extracting step).

Here, in step S1, it may determine whether or not the contact faces X, Y extracted by the contact face extracting unit 21 are contact faces having thermal resistances whose thermal conductivities have to be considered, for example, based on the type of elements connected together. This results in that analysis data including thermal conductivities of the contact faces can be generated certainly and the analysis accuracy can be improved.

Then, contact condition setting unit 23 sets contact conditions of the contact faces X, Y extracted by the contact face extracting unit 21 as described above with reference to FIGS. 6(*a*), 6(*b*), 7(*a*), and 7(*b*) (step S2; contact condition setting step).

Next, the thermal conductivity calculating unit 24 calculates thermal conductivities of the contact faces X, Y based on the contact conditions of the contact faces X, Y set in step S2 and the thermal resistance information retained in the thermal resistance information retaining unit 22 (step S3; thermal conductivity calculating step).

Here, step S3 includes a process in which the dimension calculating unit 25 calculates the dimensions of the contact faces X, Y (step S4; dimension calculating step) The thermal conductivity calculating unit 24 obtains thermal resistances of the contact faces X, Y based on the contact conditions of the contact faces X, Y and the thermal resistance information retained in the thermal resistance information retaining unit 22. The thermal conductivity calculating unit 24 further calculates thermal conductivities of the contact faces X, Y based on the obtained thermal resistance and the dimensions of the contact faces X, Y calculated by the dimension calculating unit 25 in step S4 with the use of the equation (2).

Here, regarding the contact face Y, the thermal conductivity calculating unit 24 extracts coefficient corresponding to the contact condition as thermal resistance information from the table 22*b* of the thermal resistance information retaining unit 22. As shown in the equation (1), the thermal conductivity calculating unit 24 calculates the thermal resistance of the contact face Y based on the coefficient and a predetermined standard thermal resistance.

Here, regarding the contact face X, the thermal conductivity calculating unit 24 obtains relevant thermal resistance from the table 22a of the thermal resistance information retaining unit 22 as thermal resistance information corresponding to its contact condition (adhesive material type).

Then, the generating unit 26 generates analysis data including thermal conductivities of the contact faces X, Y which are calculated in step S3 (step S5; generating step).

Here, the generating unit 26 sets (defines) the contact faces X, Y extracted by the contact face extracting unit 21 as thin films and generates analysis data by associating these thin films with the thermal conductivities of the contact faces X, Y.

The above-described steps S1 to S5 function as an analysis data generating method of the present invention.

Finally, the analyzing unit 30 implements a thermo-fluid analysis of the object 40 with the use of the analysis data of generating unit 26 of the analysis data generating unit 20 (step S6; analyzing step) and terminates the process.

As described above, according to the analysis apparatus 1 (analyzing method) of an embodiment of the present invention, the contact face extracting unit 21 extracts the contact faces X, Y (extracting step); the contact condition setting unit 23 sets contact conditions of the contact faces X, Y (contact condition setting step) thermal conductivities of the contact faces X, Y are respectably calculated based on the thermal resistance information corresponding to contact condition of the contact faces X, Y which are retained in the thermal resistance information retaining unit 22 and set by the contact condition setting unit 23 (thermal conductivity calculating step); and the generating unit 26 generates analysis data including the calculated thermal conductivities of the contact faces X, Y (generating step) Therefore, when the analysis data is generated based on the three-dimensional design data of the object 40 which is formed by a plurality of elements, thermal resistances corresponding to the contact conditions of the contact faces X, Y can be set automatically and analysis data including thermal conductivities of the contact faces X, Y can be generated accurately in a short time.

That is, according to the analysis data generating unit 20 of the present analysis apparatus 1, analysis data can be generated automatically and accurately in a short time without any manual input by an operator.

Further, since the analyzing unit 30 implements analysis based on the analysis data which is generated as described above, the analyzing unit 30 can implement a thermo-fluid analysis of the object 40 with high degree of accuracy.

Here, the generating unit 26 sets the contact faces X, Y as thin films and generates analysis data by associating the thin films with the thermal conductivities of the contact faces X, Y. Accordingly, it is possible to include the thermal conductivities in the analysis data more certainly and accurately so that an analysis result with higher degree of accuracy can be obtained by the analyzing unit 30.

Further, the thermal conductivity calculating unit 24 calculates thermal conductivities of the contact faces X, Y respectively with the use of dimensions of the contact faces X, Y calculated by the dimension calculating unit 25. Accordingly, accurate thermal conductivities corresponding to the dimensions of the contact faces X, Y can be calculated. As a result, the generating unit 26 can generate analysis data with high degree of accuracy.

The thermal resistance information retaining unit 22 retains coefficients k1, k2 corresponding to contact conditions (adhesion mode and surface condition) of inter-element connection as thermal resistance information in the table 22b. The contact condition setting unit 23 sets adhesion modes as the contact condition of the contact faces X, Y and the thermal conductivity calculating unit 24 obtains thermal resistances corresponding to the coefficients k1, k2. Accordingly, the operator can obtain thermal resistance corresponding to the adhesion mode or surface condition as the contact condition automatically without manual input. The workloads of the operator can be substantially reduced and it can prevent input errors by the operator. As a result, the generating unit 26 can implement the generation of the analysis data more accurately in a short time.

Further, the thermal resistance information retaining unit 22 retains thermal resistance corresponding to the type of adhesive material or the like used for material connection as thermal resistance information in the table 22a. The contact condition setting unit 23 sets types of adhesive materials as contact conditions of the contact faces X, Y and the thermal conductivity calculating unit 24 calculates the thermal conductivities of the contact faces X, Y based on the thermal resistances corresponding to the type of the adhesive material. Accordingly, the operator is not required to input thermal resistance manually with reference to catalog or the like, but can obtain thermal resistance corresponding to the type of the adhesive material automatically. The workloads of the operator can be significantly reduced and it can prevent input errors by the operator. As a result, the generating unit 26 can implement the generation of the analysis data more accurately in a short time.

Further, since the table 22a retains thickness corresponding to types of adhesive materials, the operator is not required to manually input thicknesses which are needed for calculating the thermal conductivity. As a result, the generating unit 26 can generate analysis data accurately in a short time.

Further, regarding the generation of the analysis data, when the generating unit 26 sets the contact faces X, Y as thin films, a thickness corresponding to type of adhesive material retained in the table 22a or a predetermined unique thickness is set automatically. Accordingly, the analysis data can be generated accurately in a short time.

[2] Others

The present invention should not be limited to the above embodiment and modifications may be made without departing from the scope of the invention.

Figure 3:
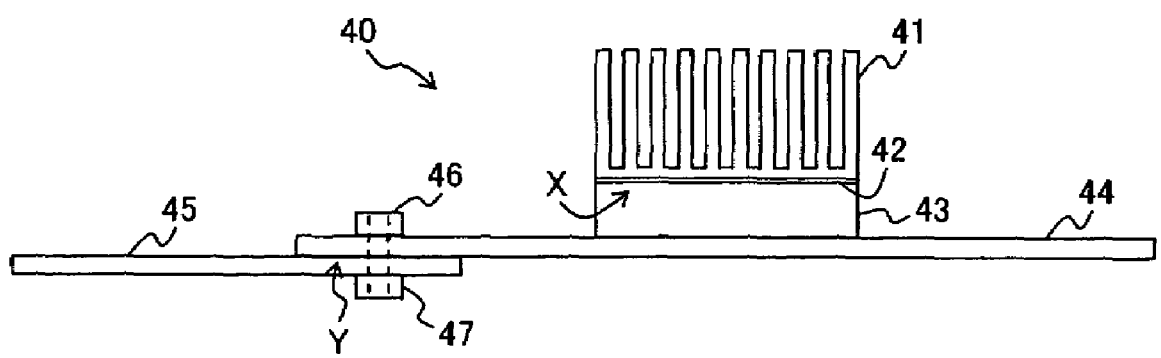
FIG. 3 is a diagram showing an example of an object as an analysis subject of the analysis apparatus according to an embodiment of the present invention.

For example, in the above-described embodiment, a case in which an object 40 shown in FIG. 3 is considered as a subject for an analysis is explained; however, it should be understood that an object considered as a subject analyzed by the present analysis apparatus 1 is not limited to an object like the object 40.

Further, the type of the contact conditions retained in thermal resistance information retaining unit 22 and the type of the contact condition set by the contact condition setting unit 23 are not limited to what is described in the above embodiment. Particularly, adhesion mode in the table 22b is not limited to the simple contact, the spring contact, and the screwed contact and may be set variously according to the object to be analyzed.

Further, according to the above-described embodiment, the table 22a of the thermal resistance information retaining unit 22 includes thicknesses corresponding to types of adhesive materials and the thermal conductivity calculating unit 24 calculates thermal conductivities based on the thicknesses in the table 22a. However, the present invention should not be limited to this. When the thermal conductivity calculating unit 24 calculates thermal conductivities corresponding to the types of the adhesive materials, thermal conductivity corresponding to the types of the adhesive materials may be calculated with the use of a predetermined common value for all types of adhesive materials.

The functions of the above-described contact face extracting unit 21, contact condition setting unit 23, thermal conductivity calculating unit 24, dimension calculating unit 25, generating unit 26, and analyzing unit 30 may be realized by a computer (including a CPU, an information processing device, and other terminals) for implementing a predetermine application program (an analyzing program or an analysis data generating program)

The program may be provided in a computer-readable recording medium such as a flexible disk, a CD (CD-ROM, CD-R, CD-RW, etc.), DVD (DVD-ROM, DVD-RAM, DVD-R, DVD-RW, DVD+R, DVD+RW, etc.). In this case, the computer reads an analyzing program or an analysis data generating program from the recording medium and transfers and stores them in an internal storage unit or an external storage unit to utilize. Further, the program may be recorded in a storage unit (recording medium) such as a magnetic disk, an optical disk, a magnetic optical disk, etc. and then it may be provided to the computer from the storage unit via a communication line.

Here, the computer should be understood that it include hardware and an OS (operating system) and it is the hardware operated under a control of the OS. Further, when hardware is operated by only the application program without the OS, the hardware itself is understood as the computer. The hardware includes at least a microprocessor such as a CPU and a means for reading the computer program recorded in a recording medium.

The application program as the analyzing program includes a program cord, in a computer as described above, for realizing functions of the contact face extracting unit 21, the contact condition setting unit 23, the thermal conductivity calculating unit 24, the dimension calculating unit 25, the generating unit 26, and the analyzing unit 30. Further, a part of the functions may be realized not by the application program but by the OS.

Further, an application program as the above-described analysis data generating program includes a program code, in a computer as described above, for realizing functions of the contact face extracting unit 21, the contact condition setting unit 23, the thermal conductivity calculating unit 24, the dimension calculating unit 25, and the generating unit 26. Further, a part of the functions maybe realized not by the application program but by the OS.

As a recording medium in the present embodiment, various computer-readable mediums may be used. For example, an IC card, a ROM cartridge, a magnetic tape, a punch card, a computer internal storage unit (memory such as RAM or ROM), an external storage unit, or a printed material with a mark such as a bar code maybe used in addition to the above-described flexible disk, CD, DVD, magnetic disk, optical disk, and magnetic optical disk.

What is claimed is:

1. An analysis data generating apparatus for generating analysis data of an object formed by a plurality of elements from three-dimensional design data of the object, comprising:
   an extracting unit for extracting a contact face where end faces of two elements contact with each other from the three-dimensional design data;
   a contact condition setting unit for setting contact condition of the contact face extracted by said extracting unit;
   a retaining unit for previously retaining thermal resistance information to obtain thermal resistance of the contact face in accordance with the contact condition of the contact face;
   a thermal conductivity calculating unit for calculating a thermal conductivity of the contact face based on the thermal resistance information which is retained in said retaining unit and corresponds to the contact condition of the contact face set by said contact condition setting unit; and
   a generating unit for generating the analysis data including the thermal conductivity calculated by said thermal conductivity calculating unit.

2. The analysis data generating apparatus according to claim 1,
   wherein said generating unit sets the contact face extracted by said extracting unit as a thin film and generates analysis data by associating the thin film with the thermal conductivity of the contact face.

3. The analysis data generating apparatus according to claim 1,
   wherein said contact condition setting unit sets a connection by adhesive material as the contact condition; and
   said retaining unit retains thermal resistance corresponding to the connection by the adhesive material which is the contact condition as the thermal resistance information.

4. The analysis data generating apparatus according to claim 3,
   wherein said retaining unit retains the thermal resistance corresponding to a type of the adhesive material.

5. The analysis data generating apparatus according to claim 1, further comprising a dimension calculating unit for calculating a dimension of the contact face extracted by said extracting unit,
   wherein said thermal conductivity calculating unit obtains thermal resistance of the contact face based on the contact condition of the contact face and the thermal resistance information and calculates the thermal conductivity of the contact face based on the obtained thermal resistance and the dimension of the contact face calculated by said dimension calculating unit.

6. The analysis data generating apparatus according to claim 5,
   wherein said retaining unit retains a coefficient corresponding to the contact condition as the thermal resistance information; and
   said thermal conductivity calculating unit obtains the thermal resistance of the contact face based on the coefficient retained in said retaining unit and a predetermined standard thermal resistance.

7. The analysis data generating apparatus according to claim 6,
   wherein said contact condition setting unit sets an adhesion mode of the contact face as the contact condition; and
   said retaining unit retains the coefficient corresponding to the adhesion mode of the contact face as the contact condition.

8. The analysis data generating apparatus according to claim 6,
   wherein said contact condition setting unit sets surface condition of the contact face as the contact condition; and
   said retaining unit retains the coefficient corresponding to the surface condition.

9. An analysis data generating method for generating an analysis data of an object formed by a plurality of elements from three-dimensional design data of the object, comprising:

an extracting step for extracting a contact face where end faces of two elements contact with each other from the three-dimensional design data;

a contact condition setting step for setting a contact condition of the contact face extracted at said extracting step;

a thermal conductivity calculating step for calculating a thermal conductivity of the contact face based on the thermal resistance information which is previously retained in a retaining unit to obtain thermal resistance of the contact face in accordance with the contact condition of the contact face and corresponds to the contact condition of the contact face set in said contact condition setting step; and a generating step for generating the analysis data including the thermal conductivity calculated in said thermal conductivity calculating step.

10. The analysis data generating method according to claim 9, wherein, in said generating step, the contact face extracted in said extracting step is set as a thin film and the analysis data is generated by associating the thin film with the thermal conductivity of the contact face.

11. The analysis data generating method according to claim 9, further comprising a dimension calculating step for calculating a dimension of the contact face extracted in said extracting step, wherein, in said thermal conductivity calculating step, thermal resistance of the contact face is obtained based on the contact condition of the contact face and the thermal resistance information and the thermal conductivity of the contact face is calculated based on the obtained thermal resistance and the dimension of the contact face calculated in said dimension calculating step.

12. The analysis data generating method according to claim 11, wherein, in said thermal conductivity calculating step, thermal resistance of the contact face is obtained based on a coefficient, which is corresponding to the contact condition as the thermal resistance information and previously retained in said retaining unit, and a predetermined standard thermal resistance.

13. A computer-readable recording medium containing an analysis data generating program for realizing, with the use of a computer, a function for generating an analysis data of an object formed by a plurality of elements from three-dimensional design data of the object, wherein the analysis data generating program instructs the computer to function as:

an extracting unit for extracting a contact face where end faces of two elements contact with each other from the three-dimensional design data;

a contact condition setting unit for setting contact condition of the contact face extracted by said extracting unit;

a thermal conductivity calculating unit for calculating a thermal conductivity of the contact face based on the thermal resistance information which is previously retained in a retaining unit to obtain thermal resistance of the contact face in accordance with the contact condition of the contact face and corresponds to the contact condition of the contact face set by said contact condition setting unit; and a generating unit for generating the analysis data including the thermal conductivity calculated by said thermal conductivity calculating unit.

14. The computer-readable recording medium containing the analysis data generating program according to claim 13, wherein the analysis data generating program instructs the computer so that said generating unit sets the contact face extracted by said extracting unit as a thin film and generates the analysis data by associating the thin film with the thermal conductivity of the contact face.

15. The computer-readable recording medium containing the analysis data generating program according to claim 13, wherein the analysis data generating program instructs the computer to function as a dimension calculating unit for calculating a dimension of the contact face extracted by said extracting unit; and the analysis data generating program instructs the computer so that said thermal conductivity calculating unit obtains thermal resistance of the contact face based on the contact condition of the contact face and the thermal resistance information and calculates the thermal conductivity of the contact face based on the obtained thermal resistance and the dimension of the contact face calculated by said dimension calculating unit.

16. The computer-readable recording medium containing the analysis data generating program according to claim 15, wherein the analysis data generating program instructs the computer so that said thermal conductivity calculating unit obtains the thermal resistance of the contact face based on a coefficient, which is corresponding to the contact condition as the thermal resistance information and previously retained in said retaining unit, and a predetermined standard thermal resistance.

* * * * *